(12) United States Patent
Sanaka

(10) Patent No.: US 6,261,588 B1
(45) Date of Patent: Jul. 17, 2001

(54) PROPHYLACTICS AND REMEDIES FOR RENAL DISEASES

(75) Inventor: Tsutomu Sanaka, Tokyo (JP)

(73) Assignee: Ricom Shoji Corp., Tokyo (JP)

( * ) Notice: Subject to any disclaimer, the term of this patent is extended or adjusted under 35 U.S.C. 154(b) by 0 days.

(21) Appl. No.: 09/411,385

(22) Filed: Oct. 4, 1999

Related U.S. Application Data

(63) Continuation of application No. PCT/JP97/01168, filed on Apr. 4, 1997.

(51) Int. Cl.$^7$ .............................. A01N 63/04; A61K 47/00
(52) U.S. Cl. ........................................... 424/439; 424/93.5
(58) Field of Search ..................................... 424/93.5, 439

(56) References Cited

U.S. PATENT DOCUMENTS 5,639,470 * 6/1997 Ishibashi et al. ..................... 424/439

FOREIGN PATENT DOCUMENTS

| 4-49244 | 2/1992 | (JP). |
| 7-2688 | 1/1995 | (JP). |

OTHER PUBLICATIONS

S.C. Tam et al, "Hypotensive and Renal Effects of an Extract of the Edible Mushroom *Pleurotus Sajor–Caju*", 1986, Life Sciences, vol. 38, pp. 1155–1161.

\* cited by examiner

*Primary Examiner*—Russell Travers
*Assistant Examiner*—Shengjun Wang
(74) *Attorney, Agent, or Firm*—Oblon, Spivak, McClelland, Maier & Neustadt, P.C.

(57) ABSTRACT

A prophylactic or a remedy for renal diseases comprises a hydrophilic solvent-extract of mushroom as an effective component. The hydrophilic solvent-extract of mushroom according to the present invention possesses an effect of markedly improving and maintaining the renal functions of undialyzed patients suffering from renal disease. Therefore, the extract permits the substantial elimination or retardation of the initiation of any dialytic therapy, which has conventionally been inevitable for the end-stage renal disease patients.

11 Claims, No Drawings

PROPHYLACTICS AND REMEDIES FOR RENAL DISEASES

This application is a Continuation of International appln. No. PCT/JP 97/01168 filed on Apr. 4, 1997.

TECHNICAL FIELD

The present invention relates to prophylactics and remedies for renal diseases and more specifically to prophylactics and remedies for renal diseases, which comprise, as an effective component, a hydrophilic solvent-extract of mushroom, prophylactics and remedies for progressive renal failure in undialyzed patients suffering from renal failure or foods having renal function-improving effect.

BACKGROUND ART

Up to this time, there has never been known any decisively effective drug for maintaining or recovering the renal function of patients suffering from end-stage renal disease and the only existing means for prolonging the life of these patients are dialytic therapy and kidney transplantation, which would force a great burden upon these patients and which are attended with a danger of death.

On the other hand, the hydrophilic solvent-extract of mushroom possesses an effect of suppressing production of, for instance, indole and scatol in feces and have accordingly been used as a deodorant, in particular, a food for deodorizing feces (see Japanese Un-Examined Patent Publication (hereunder referred to as "J.P. KOKAI") No. Hei 2-277456). However, it has never been known that the hydrophilic solvent-extract of mushroom is effective for the recovery from the symptoms of uremia, in particular, progressive renal failure in undialyzed patients suffering from end-stage renal disease.

DISCLOSURE OF THE INVENTION

Accordingly, it is an object of the present invention to provide a prophylactic or remedy for renal diseases.

It is another object of the present invention to provide a prophylactic or remedy for progressive renal failure in undialyzed patients suffering from end-stage renal disease.

It is still another object of the present invention to provide a food, which is effective for preventing or treating progressive renal failure in undialyzed patients suffering from end-stage renal disease.

It is a further object of the present invention to provide a prophylactic or remedy, in particular, a food for renal diseases, which permits the elimination or retardation of the initiation of renal dialysis in patients suffering from end-stage renal disease, whose basic treating means is diet therapy, and which can rescue patients from any irreversible loss of renal functions.

It is a still further object of the present invention to provide a prophylactic or remedy for renal diseases, which comprises a hydrophilic solvent-extract of mushroom, as an effective component.

It is a further object of the present invention to provide a method for preventing or treating renal diseases.

It is a still further object of the present invention to provide a method for preventing or treating progressive renal failure in undialyzed patients suffering from end-stage renal disease.

It is a further object of the present invention to provide a method for preventing or treating renal diseases, which permits the elimination or retardation of the initiation of dialysis therapy in patients suffering from end-stage renal disease, whose basic treating means is diet therapy, and which can rescue patients from any irreversible loss of renal functions.

According to the present invention, there is provided a prophylactic or remedy for renal diseases, which comprises a hydrophilic solvent-extract of mushroom, as an effective component.

According to another aspect of the present invention, there is provided a method for preventing or treating renal diseases, which comprises administering a hydrophilic solvent-extract of mushroom to patients who require the prevention or treatment of renal diseases.

BEST MODE FOR CARRYING OUT THE INVENTION

The inventors of this invention have used an adsorbent having a high ability of adsorbing creatinine in the intestine, while adopting, as a basic therapy, the diet therapy which makes use of a diet mainly comprising low protein content and high energy components, in order to control the progress of renal failure in chronic renal disease patients. The renal function is evaluated by the 1/Cr value in blood (reciprocal of the creatinine level in the serum; an index of the renal function; the higher the value, the lower the renal function) and the dialysis of a patient is in general started at an instance when the value reaches a level of not higher than 0.1 dl/mg.

The inventors of this invention have surprisingly found that when a hydrophilic solvent-extract of mushroom is administered to an undialyzed renal failure patient, the renal function thereof which has steadily progressed is considerably improved and that the initiation of or requirement for the dialytic therapy could be eliminated and have thus completed the present invention based on such a finding.

Thus, the present invention relates to a food for preventing or treating renal failure, which comprises a hydrophilic solvent-extract of mushroom as an effective component. The present invention also relates to a remedy for progressive renal failure, which comprises a hydrophilic solvent-extract of mushroom as an effective component.

The present invention will now be described in more detail below.

In the present invention, the term "undialyzed patient suffering from renal failure (hereunder referred to as undialyzed renal failure patient)" means a renal failure patient suffering from, for instance, chronic nephritis (or nephrosis) such as mesangial proliferative glomerulonephritis, membrane proliferative glomerulonephritis, membranaceous nephritis, lupus nephritis and diabetic nephrosis; glomerulosclerosis, nephrotic syndrome or renal ischemia, and who is not treated by the dialysis therapy. More specifically, the undialyzed uremia patients mainly means end-stage terminal renal disease patients whose degree of progressive renal failure is not less than 0.1 dl/mg and not more than 0.5 dl/mg as expressed in terms of the 1/Cr value (reciprocal of the creatinine level in the serum; an index of the renal function) or not less than 5 ml/min and not more than 70 ml/min as expressed in terms of the CCr value (creatinine clearance value; an index of renal function). These patients are appropriate subjects for the present invention.

The foregoing pathema is a condition which is on the very threshold of the initiation of the dialysis therapy, i.e., the very stage in which the renal function still remains in the patient, but it would be lost within a short period of time if leaving the patient untreated. However, a better effect would be attained if the hydrophilic solvent-extract of mushroom according to the present invention is administered even to the patient at this stage, who is subjected to the usual diet therapy. In other words, the hydrophilic solvent-extract of mushroom directly or indirectly acts on the kidney of the patient to thus markedly maintain or improve the functions of such an impaired kidney.

The hydrophilic solvent-extract of champignon mushroom (*Agaricus bisporus*) is disclosed, in detail, in J.P. KOKAI No. Hei 2-277456 (U.S. patent application Ser. No. 08/107333, now U.S. Pat No. 5,639,470; E.P. Patent No. 0381055). The mushroom per se is a food and accordingly, the hydrophilic solvent-extract thereof is not toxic at all.

The fruit body of the mushroom comprises different components depending on the maturity and specific sites thereof. It is preferred to appropriately select the growth period of the fruit body of mushroom and to properly select the extraction method depending on the sites thereof selected, in order to obtain the extract of the present invention.

The mycelia in compost also comprise effective components, but they do not provide an extract suitably used for oral ingestion, since the rate of extraction is very low and the resulting extract may contain a large amount of contaminants originated from the compost.

The fruit-body of mushroom, which is in general used as a food, is in the course of growth and has closed pileus. It is preferred, in the present invention, to use the fruit-body harvested at this stage from the viewpoint of its color tone. In the present invention, the whole fruit-body may be used, with the use of the pileus being particularly effective.

To extract effective components from the fruit-body of mushroom, it is preferred to slice up those free of any browning, i.e., fresh fruit-body or those obtained by freezing such fresh fruit-body and to then immediately put them into a hot extraction medium. The mushroom, which is cut into small pieces, may cause browning and the effective components thereof would be decomposed within a short period of time, due to the effect of phenoloxidase. For this reason, it is effective that these small pieces are immersed in an organic or inorganic acid solution having a concentration of not less than 0.1% or sprayed with such a solution in order to prevent any browning.

On the other hand, the mature mushroom whose pileus is opened may be immersed in cold water for 10 minutes to one hour to thus extract effective components thereof from the spores formed and lamellae having a dark purple color. The resulting extract initially has a deep purple color, but forms a transparent liquid through agglomeration and precipitation after allowing it to stand overnight in a cold place. This liquid is inferior in thermal stability and therefore, it is preferred to lyophilize it into powder before its practical use.

As such extraction solvents, there may be used, for instance, hydrophilic solvents such as water, methanol, ethanol, isopropyl alcohol and acetone or mixture thereof. Water or ethanol is particularly preferred since the product is used as a food and they do not cause any harmful effect even if they remain in the product. The extraction solvent is in general used in an amount ranging from 2 to 10 times (weight ratio) that of the raw material. The extraction temperature and time are suitably not less than 90° C. and not less than 30 minutes, or 80° C. and not less than 2 hours for water.

Alcohols or acetone may be used alone as such an extraction solvent, but it is preferably used in combination with water.

Moreover, the extraction solvent may comprise an organic acid or a sugar to thus ensure effective extraction of the effective components.

Examples of such organic acids preferably used herein are citric acid, malic acid, acetic acid and ascorbic acid. The amount of the organic acid to be added to the extraction solvent is preferably in the range of from 0.05 to 2% by weight while controlling the pH value of the solvent to 3.0 to 5.0.

Examples of sugars usable herein are fruit sugar, glucose, sucrose and maltose. The amount thereof to be used suitably ranges from 0.5 to 5% by weight. In this case, the effective components present within the cell wall of the spores can be extracted in a high efficiency due to the osmotic pressure of the sugar.

Moreover, it is also possible to carry out the extraction after addition of a cellulase or an amylase to water in a concentration ranging from 0.01 to 0.1% by weight to react the enzyme with the raw material at a temperature ranging from 25 to 40° C. for 2 to 24 hours and to thus decompose the cell walls or proteins of the raw material. Alternatively, the mushroom may be once frozen and then thawed to break the tissues (cell walls) and to thus ensure the effective extraction of the effective components.

The dosage form of the hydrophilic solvent-extract of mushroom is not restricted to any specific one, but the extract is most conveniently administered through the oral route. The dose thereof may vary depending on the conditions of renal diseases, age, sex or the like of the patient, but in general ranges from 0.01 to 50 g and, in particular, 0.1 to 5 g per day. The extract is continuously or intermittently administered for preferably at most 3 months, while appropriately monitoring the symptoms of the patient.

The hydrophilic solvent-extract of mushroom may be administered without any pre-treatment, but may be used or ingested in the form of a variety of foods such as drinks, gums, candies, tablets, soup, miso soup and rice gruel. The concentration of the hydrophilic solvent-extract of mushroom to be incorporated into these foods is not limited to any specific range, but may preferably be adjusted so as to ensure the amount thereof to be ingested per day as has been defined above, i.e., 0.01 to 50 g, in particular, 0.1 to 5 g per day.

INDUSTRIAL APPLICABILITY

The hydrophilic solvent-extract of mushroom according to the present invention possesses an effect of markedly improving and maintaining the renal functions of undialyzed renal failure patients and therefore, the extract permits the substantial elimination or retardation of the initiation of any dialytic therapy which has conventionally been inevitable for the end-stage renal disease patients.

EXAMPLES

The present invention will be described below in detail with reference to the following Examples.

Preparation Example 1

To 10 kg of fresh mushroom, there was added 20 kg of a 1% by weight aqueous malic acid solution to carry out the extraction at 70° C. for 70 minutes. The resulting extract (20 kg) was concentrated to a volume of 1/10 time the initial volume thereof to give 2 kg of a concentrate. Dextrin (1.64 kg) was added to the concentrate (2 kg), followed by spray-drying the resulting mixture to give 1 kg of a powdery product. Ricom Corporation sells these concentrate and powdery product under the trade name of "Champignon Extract" (registered trademark).

Example 1

This Example relates to a prophylactic or remedy for renal diseases comprising the extract (concentrate) obtained in Preparation Example 1.

Example 2

This Example relates to a prophylactic or remedy for renal diseases comprising the powdery product obtained in Preparation Example 1.

Example 3

This Example relates to a health food prepared by mixing 1 g of the powdery product of Preparation Example 1, 0.2 g of whey calcium, 0.2 g of isomalto-oligosaccharide and 0.1 g of cellulose and then formed into divided granules.

Test Example 1 (Case 1)

A subject selected in this Test Example 1 was a 24-year-old male patient suffering from chronic renal failure due to mesangial proliferative glomerulonephritis and accompanying hypertension as a complication. The patient was 170 cm in height and had a body weight of 65 kg, a CCr value of 13.2 ml/min and a 1/Cr value of 0.29 dl/mg, at the time when the administration of the "Champignon Extract" was initiated and he has been put on a diet so that the energy is limited to 2200 kcal and the protein intake is restricted to 25 g.

The powder of Preparation Example 1 was orally administered to this patient in a dose of 1 g/day for 3 months. The serum of the patient before and after the administration of the powder was inspected for the CCr value (ml/min) and the 1/Cr value (dl/mg). The results thus obtained are summarized in the following Table 1.

TABLE 1

| Time of Meas. (Date) | 1/Cr Value (dl/mg) | CCr Value (ml/min) |
| --- | --- | --- |
| 117 Days Before the Adm. (8/6) | 0.30 | 19.6 |
| 75 Days Before the Adm. (9/17) | 0.28 | 24.1 |
| 5 Days Before the Adm. (11/26) | 0.27 | 13.0 |
| 23 Days After the Adm. (12/24) | 0.27 | 13.3 |
| 75 Days After the Adm. (2/14) | 0.30 | 16.7 |
| 93 Days After the Adm. (3/4) | 0.29 | Not Determined |

The data listed in Table 1 indicate that the decrease in the 1/Cr value was suppressed and the value was kept at a level of 0.30 dl/mg, by the administration of the hydrophilic solvent-extract of mushroom. In respect of the CCr value, it was reduced from 24.1 ml/min to 13.0 ml/min during the term extending from 8 to 12 weeks before the administration of the extract, i.e., it was reduced at a rate of 5.5 ml/min/month. However, it was recognized that the value observed after the administration of the extract was apt to be improved and more specifically, it was changed from 13.3 ml/min to 16.7 ml/min, i.e., it was increased at a rate of 1.7 ml/min/month.

Test Example 2 (Case 2)

A subject selected in this Test Example 2 was a 40-year-old female patient suffering from chronic renal failure due to mesangial proliferative glomerulonephritis and developing into hypertension as a complication. The patient was 161 cm in height and had a body weight of 50 kg, a CCr value of 6.9 ml/min and a 1/Cr value of 0.19 dl/mg, at the time when the administration of the "Champignon Extract" was initiated and she has been put on a diet so that the energy is limited to 2100 kcal and the protein intake is restricted to 25 g.

The powder of Preparation Example 1 was orally administered to this patient in a dose of 1 g/day for 3 months. The serum of the patient before and after the administration of the powder was inspected for the CCr value (ml/min) and the 1/Cr value (dl/mg). The results thus obtained are summarized in the following Table 2.

TABLE 2

| Time of Meas. (Date) | 1/Cr Value (dl/mg) | CCr Value (ml/min) |
| --- | --- | --- |
| 5 Days Before the Adm. (12/19) | 0.19 | 6.9 |
| 0 Day Before the Adm. (12/24) | Not Determined | Not Determined |
| 16 Days After the Adm. (1/9) | 0.18 | 7.5 |
| 28 Days After the Adm. (2/6) | 0.18 | 7.9 |
| 56 Days After the Adm. (3/6) | 0.19 | Not Determined |

The data listed in Table 2 indicate that the 1/Cr value was maintained at a level of 0.18 dl/mg and then increased up to 0.19 dl/mg by the administration of the hydrophilic solvent-extract of mushroom. The CCr value was also increased to some extent by the administration.

Test Example 3 (Case 3)

A subject selected in this Test Example 3 was a 65-year-old male patient suffering from chronic renal failure due to nephrosclerosis and developing into hypertension as a complication. The patient was 158 cm in height and had a body weight of 54 kg, a CCr value of 37.1 ml/min and a 1/Cr value of 0.5 dl/mg, at the time when the administration of the "Champignon Extract" was initiated. Moreover, he has been put on a diet so that the energy is limited to 2200 kcal and the protein intake is restricted to 50 g.

The powder of Preparation Example 1 was orally administered to this patient in a dose of 1 g/day for 3 months. The serum of the patient before and after the administration of the powder was inspected for the CCr value (ml/min) and the 1/Cr value (dl/mg). The results thus obtained are summarized in the following Table 3.

TABLE 3

| Time of Meas. (Date) | 1/Cr Value (dl/mg) | CCr Value (ml/min) |
| --- | --- | --- |
| 116 Days Before the Adm. (8/6) | 0.55 | Not Determined |
| 74 Days Before the Adm. (11/7) | 0.51 | 30.9 |
| 0 Day Before the Adm. (12/19) | 0.52 | 37.1 |
| 35 Days After the Adm. (1/23) | 0.59 | 53.5 |
| 49 Days After the Adm. (2/6) | 0.58 | 57.5 |

The data listed in Table 3 indicate that the 1/Cr value was once increased to 0.59 dl/mg and then maintained at that level by the administration of the hydrophilic solvent-extract of mushroom. The CCr value was significantly increased to 57.5 ml/min after 49 days from the administration of the extract.

An increase of the creatinine value in serum may in general be inhibited due to the following two reasons: (1) the improvement of the ability to excrete creatinine due to the recovery of the renal function and (2) a decrease in the amount of the produced creatinine due to the reduction of the amount of muscle. However, the patient never caused any body weight reduction during the whole testing period and therefore, the decrease in the amount of the muscle is not involved in the inhibition. Accordingly, it would be concluded that the increase of the creatinine value in serum is inhibited due to the improvement of the renal function.

What is claimed is:

1. A method for preventing or treating a renal disease, which comprises orally administering a bydrophilic solvent-extract of champignon mushroom *Agaricus Bisporus* to a patient who requires the prevention or treatment of said renal disease.

2. The method of claim 1, wherein said disease is progressive renal failure in an undialyzed patient suffering from end-stage renal disease.

3. The method of claim 1, wherein said patient is undialyzed patient suffering from endstage renal disease.

4. The method of claim 1, wherein said patient suffers from at least one disorder selected from the group consisting of chronic nephritis, chronic nephrosis, mesangial proliferative glomerulonephritis, membrane proliferative glomerulonephritis, membranaceous nephritis, lupus nephritis, diabetic nephrosis, glomerulosclerosis, nephrotic syndrome and renal ischemia, and who is not treated by a dialysis therapy.

5. The method of claim 1, wherein said patient is not treated by a dialysis therapy.

6. The method of claim 1, wherein said patient suffers from endstage renal disease, and wherein said patient has a degree of progressive renal failure of not less than 0.1 dl/mg and not more than 0.5 dl/mg as expressed in terms of a 1/Cr value or said patient has a degree of progressive renal failure of not less than 5 ml/min and not more than 70 ml/min as expressed in terms of a CCr value.

7. The method of claim 1, wherein said hydrophilic solvent-extract is prepared by extracting a fruit-body of said mushroom with a hydrophilic extraction solvent.

8. The method of claim 1, wherein said administering comprises administering 0.01 to 50 g per day of said hydrophilic solvent-extract to said patient.

9. The method of claim 1, wherein said administering comprises administering 0.1 to 5 g per day of said hydrophilic solvent-extract to said patient.

10. The method of claim 1, wherein said administering is carried out continuously for at most 3 months.

11. The method of claim 1, wherein said administering is carried out intermittently for at most 3 months.

* * * * *

UNITED STATES PATENT AND TRADEMARK OFFICE
CERTIFICATE OF CORRECTION

PATENT NO. : 6,261,588 B1
DATED : July 17, 2001
INVENTOR(S) : Sanaka

It is certified that error appears in the above-identified patent and that said Letters Patent is hereby corrected as shown below:

<u>Title page,</u>
Item [73], the Assignee information should read:
-- [73] Assignee: MDF CO., LTD., Tokyo (JP) --

Signed and Sealed this

Twenty-ninth Day of January, 2002

Attest:

*Attesting Officer*

JAMES E. ROGAN
*Director of the United States Patent and Trademark Office*